(12) United States Patent
Nishizawa et al.

(10) Patent No.: US 7,507,966 B2
(45) Date of Patent: Mar. 24, 2009

(54) OPTICAL-PATH-DIFFERENCE COMPENSATION MECHANISM FOR ACQUIRING WAVE FORM SIGNAL OF TIME-DOMAIN PULSED SPECTROSCOPY APPARATUS

(75) Inventors: Seizi Nishizawa, Hamura (JP); Toshiyuki Iwamoto, Hachioji (JP)

(73) Assignees: Japan Science and Technology Agency, Saitama (JP); Seizi Nishizawa, Tokyo (JP)

( * ) Notice: Subject to any disclaimer, the term of this patent is extended or adjusted under 35 U.S.C. 154(b) by 447 days.

(21) Appl. No.: 10/568,528

(22) PCT Filed: Aug. 19, 2004

(86) PCT No.: PCT/JP2004/011926

§ 371 (c)(1),
(2), (4) Date: Feb. 17, 2006

(87) PCT Pub. No.: WO2005/019809

PCT Pub. Date: Mar. 3, 2005

(65) Prior Publication Data

US 2006/0278830 A1    Dec. 14, 2006

(30) Foreign Application Priority Data

Aug. 22, 2003    (JP)    ............... 2003-299373

(51) Int. Cl.
*G01J 5/02*    (2006.01)
(52) U.S. Cl. ............... 250/339.07; 250/341.1
(58) Field of Classification Search ............ 250/339.09, 250/341.1, 458.1, 339.07
See application file for complete search history.

(56) References Cited

U.S. PATENT DOCUMENTS

| 5,227,861 A * | 7/1993 | Nishizawa et al. ......... 356/497 |
| 6,078,047 A | 6/2000 | Mittleman et al. |
| 2002/0067480 A1 | 6/2002 | Takahashi |

FOREIGN PATENT DOCUMENTS

| JP | 5-115485 A | 5/1993 |
| JP | 11-108845 A | 4/1999 |
| JP | 2000-275105 A | 10/2000 |

(Continued)

OTHER PUBLICATIONS

Iwamoto, Chemical Industry, vol. 54, No. 8, pp. 36-41, (Aug. 1, 2003).

(Continued)

*Primary Examiner*—David P Porta
*Assistant Examiner*—Mark R Gaworecki
(74) *Attorney, Agent, or Firm*—Birch, Stewart, Kolasch & Birch, LLP

(57) ABSTRACT

A time-domain pulsed spectroscopy apparatus which has a pulsed laser light source; a splitting unit to split pulsed laser light; a pulsed-light emitting unit; a detector; a sample holder; and a sample-unit entrance and exit optical systems; wherein the time-domain pulsed spectroscopy apparatus further comprises: at least one optical-path-length varying unit for setting a photometric range; at least one optical delay unit for the wave form signal measurement; and, at least one gate member to pass or block the pulsed light to a reflector.

8 Claims, 7 Drawing Sheets

FOREIGN PATENT DOCUMENTS

| | | | |
|---|---|---|---|
| JP | 2000275105 A | * | 10/2000 |
| JP | 2001-21503 A | | 1/2001 |
| JP | 2001-66375 A | | 3/2001 |
| JP | 2001-141567 A | | 5/2001 |
| JP | 2001-275103 A | | 10/2001 |
| JP | 2002-98634 A | | 4/2002 |
| JP | 2002-243416 A | | 8/2002 |
| JP | 2002-257629 A | | 9/2002 |
| JP | 2002-277393 A | | 9/2002 |
| JP | 2002-277394 A | | 9/2002 |
| JP | 2003-14620 A | | 1/2003 |
| JP | 2003-75251 A | | 3/2003 |
| JP | 2003-83888 A | | 3/2003 |
| JP | 2003-121355 A | | 4/2003 |
| JP | 2003-131137 A | | 5/2003 |
| WO | WO-00/50859 A1 | | 8/2000 |
| WO | WO-00/79248 A1 | | 12/2000 |
| WO | WO-02/075291 A1 | | 9/2002 |
| WO | WO-03/058212 A1 | | 7/2003 |
| WO | WO-03/102557 A1 | | 12/2003 |

OTHER PUBLICATIONS

Kojima et al., Journal of The Spectroscopial Society of Japan, vol. 52, No. 2, pp. I 69-81, (Dec. 25, 2002).

Sakai, Journal of The Spectroscopical Society of Japan, vol. 50, No. 6, Supplement, pp. 261-273, (Oct. 22, 2001).

Tani et al., Applied Optics, vol. 36, No. 30, (Oct. 20, 1997).

Wu et al., Applied Physics Letters, vol. 67, No. 24, pp. 3523-3525, (Dec. 11, 1995).

S. Kojima et al. Journal of Molecular Structure, vols. 651-653, Jun. 1, 2003, cover page and pp. 285-288.

* cited by examiner

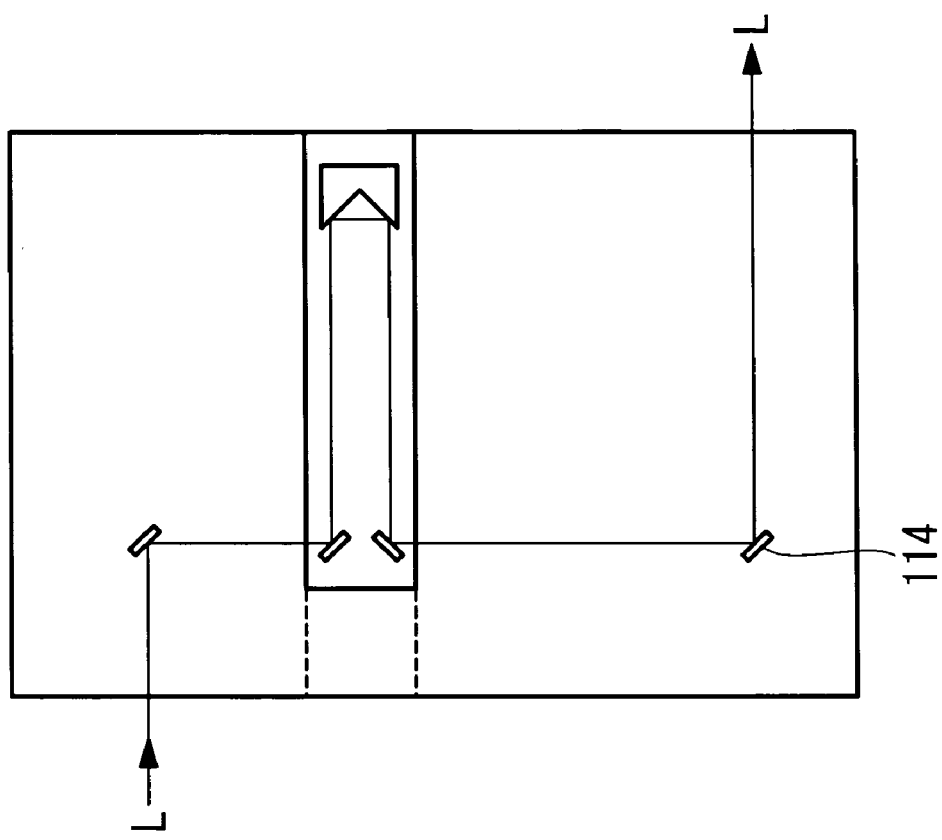
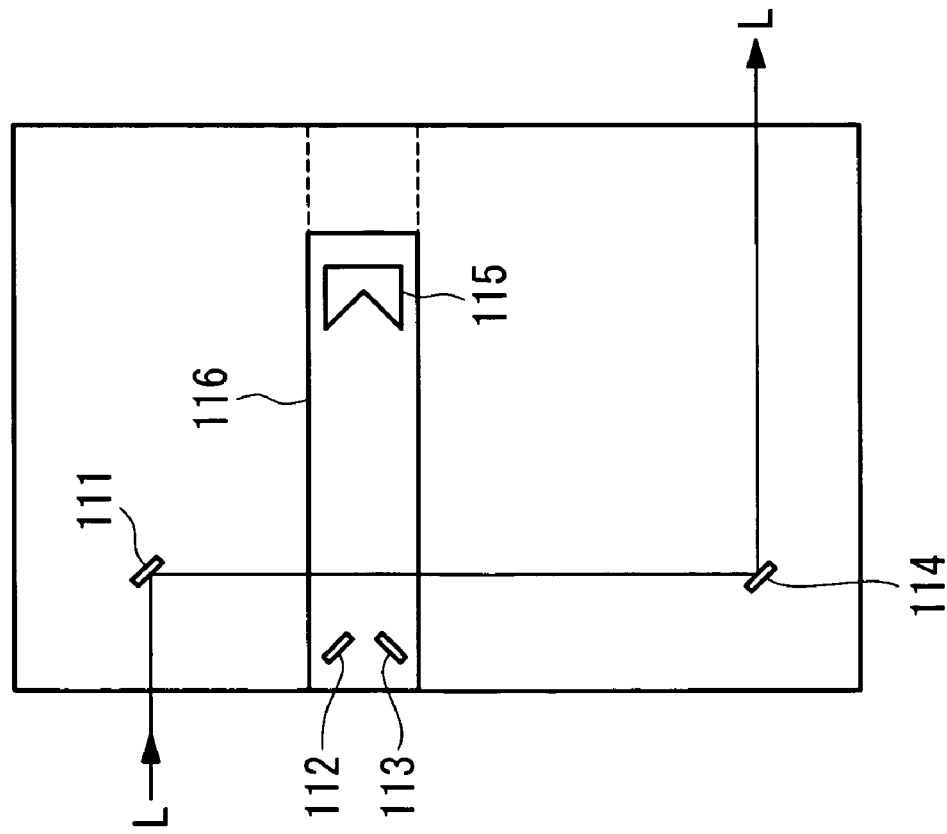

OPTICAL-PATH-DIFFERENCE COMPENSATION MECHANISM FOR ACQUIRING WAVE FORM SIGNAL OF TIME-DOMAIN PULSED SPECTROSCOPY APPARATUS

TECHNICAL FIELD

The present invention relates to a time-domain pulsed spectroscopy apparatus, and in particular, to a scanning mechanism and optical system alignment structure (optical arrangement) for acquiring a wave form signal thereof.

BACKGROUND ART

Due to the practical adoption of ultrashort pulsed laser technology in recent years, emission techniques and detection techniques for pulsed, coherent, far-infrared (particularly in the terahertz region) electromagnetic waves have progressed rapidly. Accordingly, time-domain pulsed spectroscopy using these pulsed far-infrared electromagnetic waves has become possible, and the pioneering development of practical time-domain pulsed spectroscopy apparatuses has progressed in Japan too.

Time-domain pulsed spectroscopy is a spectroscopy method in which, by measuring the time-dependent electric field intensity of the pulsed electromagnetic field and by Fourier transforming this time-dependent data (time-series data), the electric field intensity and phase of individual frequency components forming this pulse are obtained. One feature of this spectroscopy method is that the measurement wavelength range is the boundary region between light and electromagnetic waves, which is difficult to achieve with conventional measurement. Therefore, this spectroscopy method is expected to elucidate the properties of novel materials and new phenomena. Furthermore, only the electric field intensity of an electromagnetic wave can be obtained with conventional spectroscopy methods; however, this time-domain pulsed spectroscopy method has the unique feature that, by directly measuring temporal changes in the electric field intensity of electromagnetic waves, it can obtain not only the electric field intensity (amplitude) of the electromagnetic waves, but also the phase thereof. Therefore, it is possible to obtain a phase-shift spectrum by comparison with a case where there is no sample. Because the phase shift is proportional to the wave vector, it is possible to determine the dispersion relation in the sample using this spectroscopy method, and it is also possible to determine the dielectric constant of a dielectric from this dispersion relation (see Japanese Unexamined Patent Application Publication No. 2002-277394).

FIG. 1 shows one example of a conventional time-domain pulsed spectroscopy apparatus.

Reference numeral 1 is a light source for emitting femtosecond laser. Femtosecond laser light L1 emitted from the light source 1 is split at a beam splitter (splitting unit) 2. One of the femtosecond lasers is radiated onto a pulsed-light emitting unit 5 as excitation pulsed laser light (pump pulsed light) L2. At this time, after being modulated by an optical chopper 3, the excitation pulsed laser light L2 is focused by an objective lens 4. This pulsed-light emitting unit 5 is, for example, a photoconductive element in which an electric current flows momentarily when the excitation pulsed laser light L2 is radiated, and emits a far-infrared electromagnetic pulse. This far-infrared electromagnetic pulse is guided by parabolic mirrors and is irradiated onto a measurement sample 8. Reflected or transmitted pulsed electromagnetic waves (in this example, transmitted pulsed electromagnetic waves) from the sample 8 are guided to a detector 12 by parabolic mirrors 9 and 10.

The other laser light split at the beam splitter 2 is guided to the detector 12 as detection pulsed laser light (sampling pulsed light) L3. This detector 12, which is also, for example, a photoconductive element, becomes conductive only for the instant when the detection pulsed laser light L3 is irradiated; therefore, it is possible to detect the electric field intensity of the reflected or transmitted pulsed electromagnetic waves from the sample 8, arriving at that instant, as an electrical current. A wave form signal of the electric field intensity of the reflected or transmitted pulsed electromagnetic waves from the sample 8 can be obtained by applying a delay time at predetermined time intervals to the detection pulsed laser light L3 with respect to the excitation pulsed laser light L2 using an optical delay unit 13 (or 14). In this example, in addition to the optical delay unit 13 (or 14) for wave form signal measurement, an optical delay unit 14 (or 13) for adjusting the temporal origin is also provided.

Each item of time-resolved data of the electric field intensity of the reflected or transmitted electromagnetic waves from the sample 8 is processed by a signal processing unit. More specifically, the data is transferred to a computer 17 via a lock-in amplifier 16 and is then stored as time-series data, and amplitude and phase spectra of the electric field intensity of the reflected or transmitted electromagnetic waves from the sample 8 are obtained by applying Fourier transform processing to one sequence of time-series data in the computer 17 to transform it into vibration-frequency (frequency) space.

[Patent Document 1] Japanese Unexamined Patent Application Publication No. 2003-131137.
[Patent Document 2] Japanese Unexamined Patent Application Publication No. 2003-121355.
[Patent Document 3] Japanese Unexamined Patent Application Publication No. 2003-83888.
[Patent Document 4] Japanese Unexamined Patent Application Publication No. 2003-75251.
[Patent Document 5] Japanese Unexamined Patent Application Publication No. 2003-14620.
[Patent Document 6] Japanese Unexamined Patent Application Publication No. 2002-277393.
[Patent Document 7] Japanese Unexamined Patent Application Publication No. 2002-277394.
[Patent Document 8] Japanese Unexamined Patent Application Publication No. 2002-257629.
[Patent Document 9] Japanese Unexamined Patent Application Publication No. 2002-243416.
[Patent Document 10] Japanese Unexamined Patent Application Publication No. 2002-98634.
[Patent Document 11] Japanese Unexamined Patent Application Publication No. 2001-141567.
[Patent Document 12] Japanese Unexamined Patent Application Publication No. 2001-66375.
[Patent Document 13] Japanese Unexamined Patent Application Publication No. 2001-21503.
[Patent Document 14] Japanese Unexamined Patent Application Publication No. 2001-275103.
[Non-patent Document 1] Q. Wu and X.-C. Zhang, Appl. Phys. Lett. 67 (1995) 3523).
[Non-patent Document 2] M. Tani, S. Matsuura, K. Sakai, and S. Nakashima, Appl. Opt. 36 (1997) 7853.
[Non-patent Document 3] Kiyomi SAKAI, Bunko Kenkyu (Spectroscopy), 50 (2001) 261. [Non-patent Document 4]

Seiji KOJIMA, Seiji NISHIZAWA, and Mitsuo TAKEDA, Bunko Kenkyu (Spectroscopy), 52 (2003) 69.

DISCLOSURE OF INVENTION

The above time-domain pulsed spectroscopy apparatus is not limited to including the far-infrared wavelength region in the spectroscopic measurement range, which is difficult using a conventional spectroscopy apparatus, and can independently measure not only the intensity distribution but also the phase distribution in the measurement spectra thereof. Furthermore, time-resolved spectroscopy for observing a picosecond-domain transient phenomenon in real-time is also possible. Due to the provision of such features, the type, state (solid, liquid, gas, etc.) and so on of samples that can be measured or that are desired to be measured with the time-domain pulsed spectroscopy apparatus cover a wide range. However, in order to carry out time-domain spectroscopy of such a wide range of samples and states thereof, different optical systems or optical arrangements are required accordingly, and therefore, there is a drawback in that a substantial burden is placed on the operator and, in addition, a long time is required for preparation and so on until measurement starts, after replacing the sample.

Therefore, the present invention has been conceived in light of the circumstances described above, and it is an object thereof to provide a time-domain pulsed spectroscopy apparatus that can perform time-domain pulsed spectroscopy of a variety of samples and states thereof, easily and in a short period of time.

In order to achieve the object described above, the present invention employs the following configurations.

A time-domain pulsed spectroscopy apparatus of the present invention comprises a pulsed laser light source; a splitting unit configured to split pulsed laser light from the pulsed laser light source into excitation pulsed laser light and detection pulsed laser light; a pulsed-light emitting unit configured to emit pulsed light including wavelengths in the far-infrared wavelength region due to irradiation of the excitation pulsed laser; a detector configured to detect a wave form signal of the electric field intensity of reflected or transmitted pulsed light from the sample onto which the pulsed light from the pulsed-light emitting unit is radiated; a sample holder configured to hold the sample; and sample-unit entrance and exit optical systems configured to guide the pulsed light from the pulsed-light emitting unit to the sample and to guide to the detector pulsed light reflected from or transmitted through the sample due to the irradiation; wherein the time-domain pulsed spectroscopy apparatus further comprises at least one optical-path-length varying unit for setting a photometric range, disposed in an incident-side optical path from the splitting unit to the pulsed-light emitting unit and/or in a detection-side optical path from the splitting unit to the detector; and at least one optical delay unit for the wave form signal measurement, disposed in the incident-side optical path from the splitting unit to the pulsed-light emitting unit and/or in the detection-side optical path from the splitting unit to the detector.

Here, "sample-unit entrance and exit optical systems" are optical systems including optical systems before and after a sample for which replacement and adjustment of the optical systems and/or changing and adjustment of the optical arrangement is necessary when changing the type or state of the sample, and means optical systems disposed between the pulsed-light emitting unit and the detector.

"Optical-path-length varying unit for setting a photometric range" is a device for compensating for changes in the optical path length when the optical path lengths of the sample-unit entrance and exit optical systems change due to replacement of the optical systems and/or variations in the optical arrangement as a result of changing, for example, the type or state of the sample, and for setting the measurement start position of the wave form signal of the electric field intensity of a pulsed electromagnetic wave reflected from or transmitted through the sample. In particular, it means a device having a configuration that can compensate for large changes in the optical path length, for example, simply by scanning a reflector, even for large changes in the optical path length as a result of replacing the optical system.

The variation in optical path length by the optical-path-length varying unit may be achieved by a configuration that can vary sequentially it or a configuration that can vary it non-sequentially. In other words, it may be a configuration that sequentially varies the optical path length by, for example, scanning a reflector disposed in the optical path, or alternatively, it may be a configuration in which an optical path for which the photometric range is set for one sample is switched by means of a reflecting mirror and changed to an optical path that sets the photometric range for another sample.

"Optical delay unit for wave form signal measurement" is a device in which each optical delay unit has the same functionality as the conventional optical delay unit for wave form signal measurement (reference numerals 13 and 14 in FIG. 1); however, when multiple optical delay units are provided, it differs from the conventional optical delay unit in that it has a configuration capable of measuring a wave form signal over a period of time that is increased according to the number of optical delay units.

It goes without saying that various arrangements are possible for the "optical-path-length varying unit for setting a photometric range" and the "optical delay unit for wave form signal measurement", regardless of whether they are parallel arrangements or series arrangements.

According to the present invention, when the optical path length of the sample-unit entrance and exit optical systems changes, an advantage is provided in that it is possible to compensate for that change in optical path length and to set the measurement starting position of a wave form signal of the electric field intensity of a reflected or transmitted pulsed electromagnetic wave from the sample. In particular, even for a large change in optical path length as a result of replacing the optical system, an advantage is afforded in that it is possible to compensate for that large change in optical path length using the optical-path-length varying unit for setting the measurement range. A further advantage is provided in that the photometric range can be freely set. When a plurality of optical delay units for wave form signal measurement are provided, an advantage is provided in that measurement of the wave form signal is possible over a time period that is increased by an amount according to the number of optical delay units.

Furthermore, in the time-domain pulsed spectroscopy apparatus of the present invention, the optical-path-length varying unit for setting a photometric range is a movable reflector.

The "movable reflector for setting the photometric range" is a reflector of the type that can vary the optical path length typically by scanning, but it may be based on a technology that is completely different from the conventional reflector (reference numeral 13 or 14 in FIG. 1) for adjusting the temporal origin, required as a result of adjusting the optical arrangement. In other words, regarding the actual difference in configuration, because the conventional reflector for adjusting the temporal origin adjusts the temporal origin which is shifted in optical adjustment carried out during measurement, and it does not matter if the scanning range of the reflector is reduced, it is sufficient to provide a single reflector. With the apparatus, by also providing the function for adjusting the temporal origin in the "optical delay unit for wave form signal measurement", there are some cases where a reflector for adjusting the temporal origin need not be independently provided, which means that the reflector for adjusting the temporal origin is not an essential component. Accordingly, the movable reflector for setting the photometric range in the present invention is an essential component of the present invention and enables even large variations in the optical path length to be compensated for; therefore, a noticeably wider scanning range combining one, two, or more movable reflectors for setting the photometric range is formed compared with the reflector for adjusting the temporal origin. Therefore, providing a larger number of reflectors results in a configuration that is capable of widening the scanning region even more. Accordingly, the movable reflector for setting the photometric range in the present invention features an operating method that is completely different from the conventional one for a scannable reflector, and can thus be considered advantageous in that it enables simple measurement merely by scanning the reflector for setting the photometric range, even for a wide range of samples for which a large change in optical path length is unavoidable.

Furthermore, the "movable reflector for setting the photometric range" is a structure in which, by disposing a plurality of reflectors in parallel when the scanning distance of one reflector cannot be increased above an upper size limit, it is possible to ensure a longer optical path length by an amount corresponding to the number of these reflectors.

It goes without saying that the "movable reflector for setting the photometric range" is not limited to setting the measurement start position of the wave form signal but can also be used for adjusting the temporal origin, and it can be used to set various photometric ranges which require changes in the optical path length.

The "movable reflector for setting the measurement range" is a reflecting mirror such as a corner cube mirror, for example, but it is not limited thereto.

According to the present invention, an advantage is provided in that it is possible to continuously vary the optical path length.

In the time-domain pulsed spectroscopy apparatus of the present invention, the optical-path-length varying unit for setting a measurement range is a movable or fixed reflector; and either reflector includes, at the incident side of the pulsed light to the reflector, a gate member configured to pass or block the pulsed light to the reflector, and by switching between passing or blocking, it is possible to add an optical path via one, two, or more of the reflectors to extend the optical path length and/or to skip one, two, or more of the reflectors to shorten the optical path length.

The gate member is, for example, a reflecting mirror and switches the optical path of the pulsed light by inserting and removing this reflecting mirror into and from the optical path to vary the optical path length. In other words, by inserting and removing the reflecting mirror, the pulsed light is incident on a predetermined reflector or blocked, and the optical path via that reflector can be added to extend the optical path length, or that reflector can be skipped to reduce the optical path length.

The gate member may be configured to pass and block the pulsed light without moving it spatially.

The switching between passing and blocking states of the gate member may be automatic or manual, and variation of the optical path length may be carried out by a plurality of gate members.

According to the present invention, an advantage is provided in that it is possible to vary the optical path length without moving the reflector spatially. In other words, an advantage is provided in that, since the optical path length can be varied even with a fixed reflector, it is possible to construct a low-cost apparatus. An advantage is also provided in that it is possible to select a reflector to be used from among a plurality of reflectors, and it is possible to freely set the optical path according to the measurement. Therefore, an advantage is afforded in that it is possible to select a reflector to be used and to perform measurement for each measurement of the same sample, not just each time the sample is replaced. Furthermore, when a problem occurs with one, two, or more reflectors of the plurality of reflectors, an advantage is afforded in that it is also possible to replace that reflector and set the optical path. Moreover, an advantage is afforded in that a wider range of arrangements is possible in terms of the optical arrangement of the optical system involving a plurality of reflectors.

Furthermore, in the time-domain pulsed spectroscopy apparatus of the present invention, passing or blocking of at least one of the gate members is performed by inserting and removing the gate member, by translational motion, into and from the optical path.

The gate member may be configured to be translated together with the reflector.

Furthermore, in the time-domain pulsed spectroscopy apparatus of the present invention, passing or blocking of at least one of the gate members is performed by inserting and removing the gate member, by rotation, into and from the optical path.

Here, the term "rotation" includes all cases where the optical path switching operation can be accomplished by rotationally driving the gate member.

Furthermore, the time-domain pulsed spectroscopy apparatus of the present invention further includes a driving device configured to automatically scan the optical-path-length varying unit and/or the optical delay unit; and a computer control apparatus configured to automatically control the driving device.

Here, as the "driving device", it is possible to use a standard driving device for scanning, such as a stepping motor, for example.

According to the present invention, an advantage is provided in that it is possible to automatically scan the optical-path-length varying unit and/or the optical delay unit, and the scanning thereof can be automatically controlled by the computer.

Furthermore, in the time-domain pulsed spectroscopy apparatus of the present invention, the sample holder and the sample-unit entrance and exit optical systems are provided inside an auxiliary optical unit that can be attached to enable replacement thereof.

The auxiliary optical unit is preferably a specialized unit provided with sample-unit entrance and exit optical systems with optimum designs for each sample.

With this time-domain pulsed spectroscopy apparatus, the spatial dimensions of the apparatus equipped with the auxiliary optical unit can be set within a range that allows changes in the optical path length to be corrected by the scannable reflector for setting the photometric range. Therefore, the spatial dimensions are, for example, a width of 150 mm or more, a depth of 180 mm or more, and a height of 150 mm or more.

According to the present invention, because a large change in the optical path length as a result of replacing the auxiliary optical unit can be compensated using the optical-path-length varying unit for setting the photometric range, an advantage is provided in that the preparation time until commencement of measurement can be reduced. Also, by using a specialized auxiliary optical unit provided with sample-unit entrance and exit optical systems having optimum designs for each sample, an advantage is afforded in that it is not necessary to adjust the sample-unit entrance and exit optical systems when replacing the auxiliary optical unit.

Furthermore, the time-domain pulsed spectroscopy of the present invention has an optical design such that provides optical alignment with respect to the auxiliary optical unit.

Here, the term "provides optical alignment" means that the FOV (Field of View) Values Match.

According to the present invention, an advantage is afforded in that it is possible to prevent light loss at the connection portion between the auxiliary optical unit and the apparatus, even as a result of replacing the auxiliary optical unit.

Furthermore, in a time-domain pulsed spectroscopy apparatus comprising a pulsed laser light source; a splitting unit configured to split pulsed laser light from the pulsed laser light source into excitation pulsed laser light and detection pulsed laser light; a pulsed-light emitting unit configured to emit pulsed light including wavelengths in the far-infrared wavelength region due to irradiation of the excitation pulsed laser; a detector configured to detect a wave form signal of the electric field intensity of reflected or transmitted pulsed light from the sample onto which the pulsed light from the pulsed-light emitting unit is radiated; a sample holder configured to hold the sample; and sample-unit entrance and exit optical systems configured to guide the pulsed light from the pulsed-light emitting unit to the sample and to guide pulsed light reflected from or transmitted through the sample due to the irradiation towards the detector; the present invention is characterized in that, from the pulsed-light emitting unit to the sample-unit entrance and exit optical systems and/or from the detector to the sample-unit entrance and exit optical systems, one or a plurality of planar mirrors and one or a plurality of aspherical mirrors are disposed in this order.

The aspherical mirror disposed in the incident-side optical path between the pulsed-light emitting unit and the sample-unit entrance and exit optical systems converges the pulsed light towards the sample. On the other hand, the planar mirror is disposed between the pulsed-light emitting unit and the aspherical mirror and deflects the pulsed light emitted from the pulsed-light emitting unit. Therefore, the optical path length of the pulsed-light emitting unit and the aspherical mirror can be increased. By increasing this optical path length, it is possible to reduce, as much as possible, the focal area focused by the aspherical mirror, and consequently, it is possible to increase the spatial resolution of the sample to be measured.

Also, because the pulsed light is deflected at the planar mirror, it is possible, as well as increasing the optical path length, to make the apparatus configuration extremely compact.

Because the optical path length of the pulsed-light emitting unit and the aspherical mirror can be increased, it is possible make the distance between the aspherical mirror and the sample large, while maintaining a desired focal area. Therefore, sufficient space can be ensured around the sample, in other words, space for the sample-unit entrance and exit optical systems and the sample holder, thus allowing the degree of freedom for the analysis procedure to be increased.

In the same way as the incident-side optical path described above, the detection-side optical path between the detector and the sample-unit entrance and exit optical systems has a configuration in which a planar mirror is disposed between the aspherical mirror and the detector to increase the optical path length; therefore, it is possible to reduce, as much as possible, the focal area of the beam focused by the aspherical mirror, and consequently, it is possible to increase the spatial resolution of the sample to be measured.

BRIEF DESCRIPTION OF DRAWINGS

[FIG. 7](a) Outline configuration diagram of another embodiment of an optical-path-difference compensation mechanism for wave form signal acquisition in the time-domain pulsed spectroscopy apparatus of the present invention. (b) Diagram showing a case where gate members and a reflector in (a) are moved.

Figure 1:
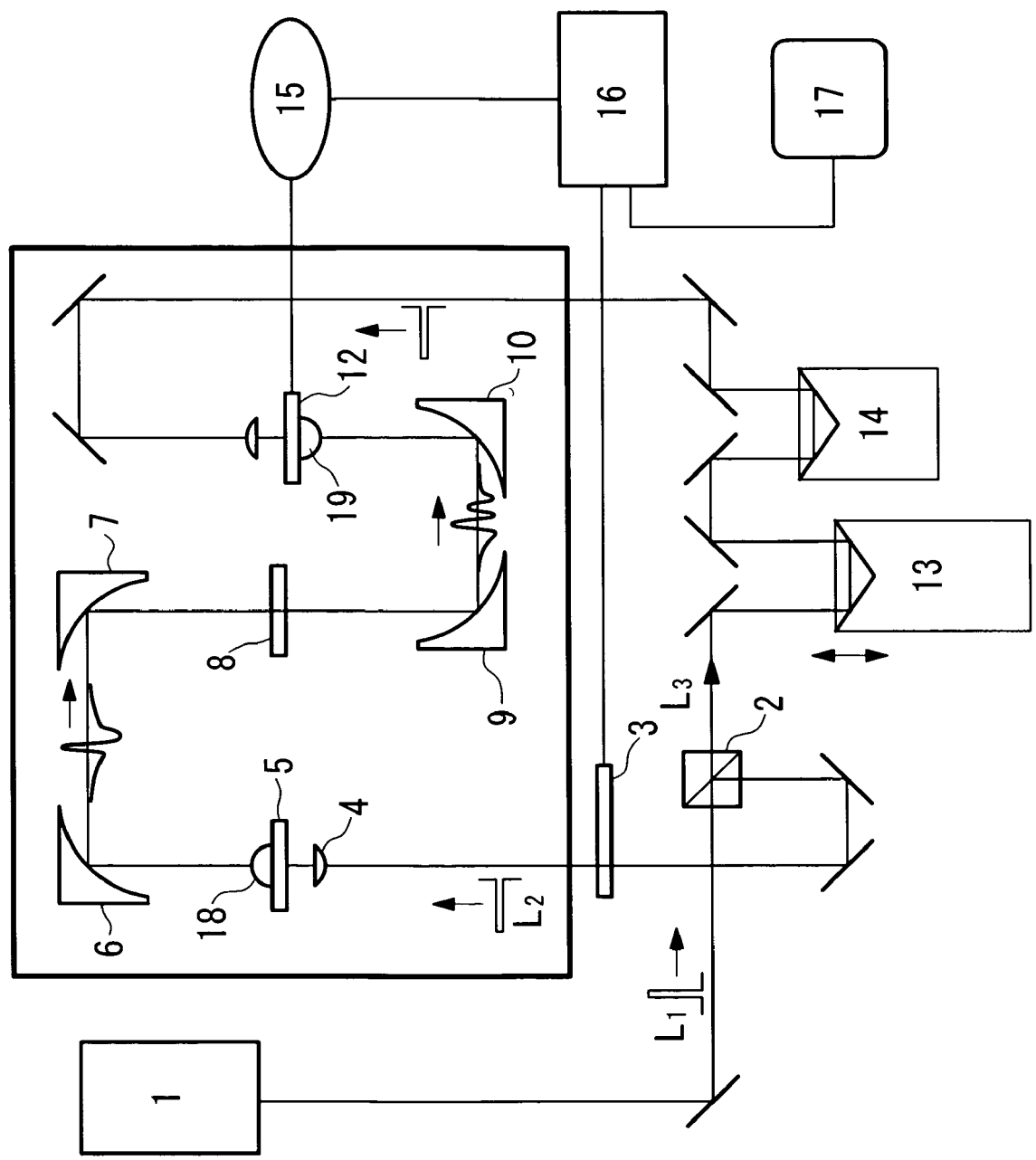
[FIG. 1] Outline configuration diagram of a conventional time-domain pulsed spectroscopy apparatus.

REFERENCE NUMERALS 1 pulsed laser light source
2 splitting unit
8 sample
12 detector
20 time-domain pulsed spectroscopy apparatus
26, 27, 28, 29 aspherical mirror
30 auxiliary optical unit
31 sample holder unit
32, 33, 34 sample-unit entrance optical system
35, 36, 37 sample-unit exit optical system
41, 42 optical-path-length varying unit or optical delay unit
51, 52, 53 reflector
61, 62, 63, 64 reflector
71, 73, 75 gate member
81, 82, 83 reflector
91, 93 gate member
101, 102 reflector 112 gate member
115 reflector

BEST MODE FOR CARRYING OUT THE INVENTION

Figure 2:
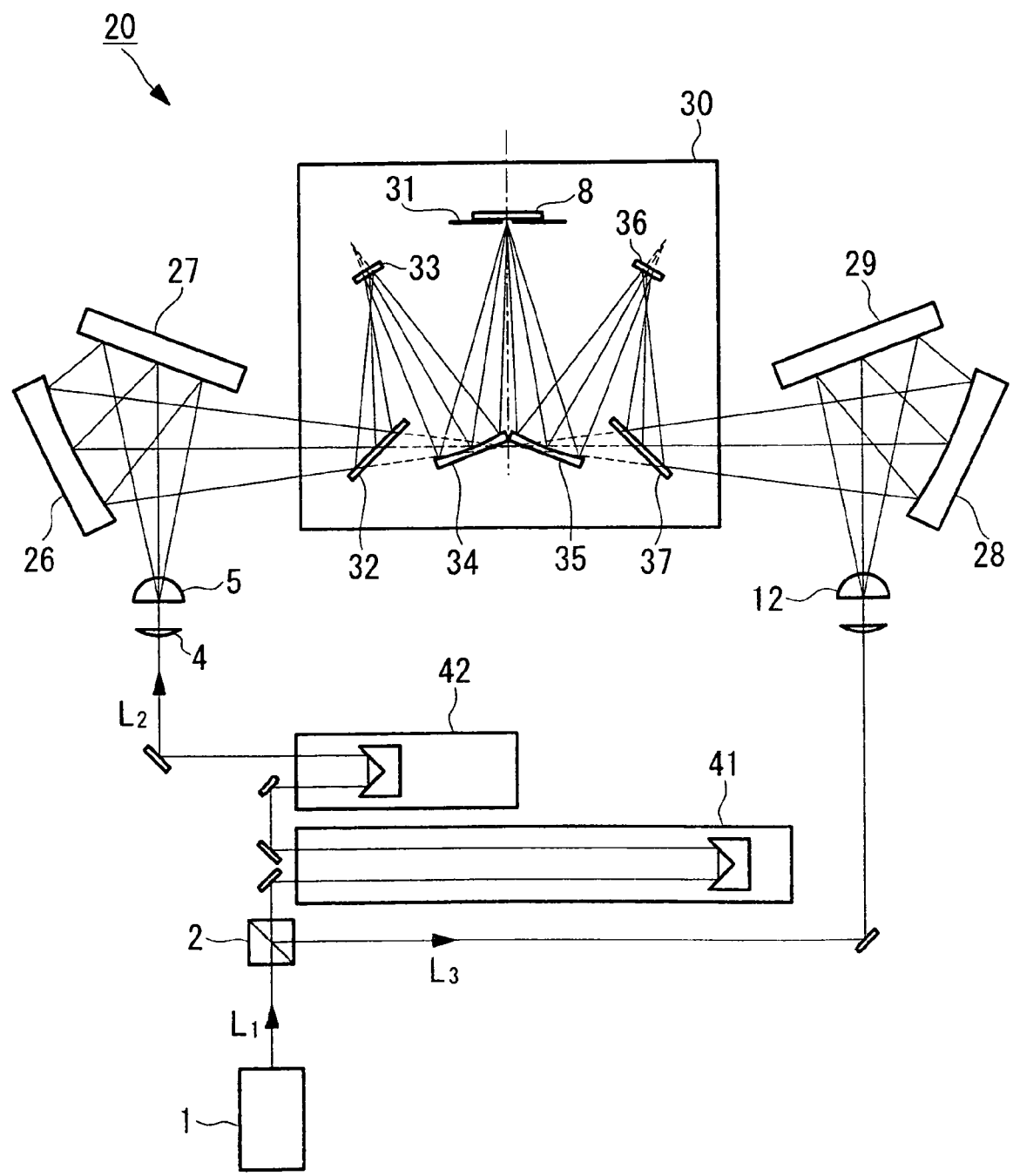
[FIG. 2] Outline configuration diagram of one embodiment of a time-domain pulsed spectroscopy apparatus of the present invention.

FIG. 2 shows the outline configuration of an embodiment of a time-domain pulsed spectroscopy apparatus and an optical-path-difference compensation device for wave form signal acquisition. The same constituent elements as those in FIG. 1 are assigned the same reference numerals and a description thereof is omitted.

This time-domain pulsed spectroscopy apparatus 20 includes a pulsed laser light source 1. Pulsed laser light L1 from this pulsed laser light source 1 is guided to a splitting unit 2 that splits it into excitation pulsed laser light L2 and detection pulsed laser light L3.

The time-domain pulsed spectroscopy apparatus 20 further includes a pulsed-light emitting unit 5 that emits pulsed light including wavelengths in the far-infrared wavelength region upon being irradiated with the excitation pulsed laser L2 and a detector 12 for detecting a wave form signal of the electric field intensity of reflected pulsed light from a sample 8, which is irradiated with the pulsed light from this pulsed-light emitting unit 5.

Between the pulsed-light emitting unit 5 and the detector 12 are provided a sample holder 31 for holding the sample 8; a sample-unit entrance optical system 32, 33, and 34 for conveying pulsed light from the pulsed-light emitting unit to the sample; and a sample-unit exit optical system 35, 36, and 37 for conveying pulsed light reflected from the sample due to this irradiation towards the detector 12.

Furthermore, the time-domain pulsed spectroscopy apparatus 20 includes at least one optical-path-length varying unit (a corner cube mirror in the case of FIG. 2) 41 for setting a photometric range and at least one optical delay unit 42 (a corner cube mirror in the case of FIG. 2) for wave form signal measurement. Here, the optical-path-length varying unit 41 is a movable reflector that can be scanned.

Driving devices (not shown in the drawing) for automatic scanning are provided in the optical-path-length varying unit 41 for setting the photometric range and in the optical delay unit 42 for wave form signal acquisition, and in addition, a computer control apparatus (not shown in the drawing) for automatically controlling these driving devices is provided. (However, regarding the reflectors 41 and 42, it is also acceptable that the former is used for wave form signal measurement and the latter is used for setting the photometric range.)

Furthermore, the sample holder 31 and the sample-unit entrance and exit optical systems 32, 33, 34, 35, 36, and 37 are provided inside an auxiliary optical unit 30, which can be detached from the time-domain pulsed spectroscopy apparatus and replaced.

An ellipsoidal mirror (aspherical mirror) 26 and a planar mirror 27, serving as optical elements, are provided in the incident-side optical path between the pulsed-light emitting unit 5 and the auxiliary optical unit 30. The ellipsoidal mirror 26 converges the pulsed light from the pulsed-light emitting unit 5. The planar mirror 27 is located between the pulsed-light emitting unit 5 and the ellipsoidal mirror 26 and serves to deflect the pulsed light from the pulsed-light emitting unit 5. There may be one ellipsoidal mirror 26 and one planar mirror 27, as in the present embodiment, or a plurality thereof may be combined.

An ellipsoidal mirror (aspherical mirror) 28 and a planar mirror 29, serving as optical elements, are provided in the detection-side optical path between the detector 12 and the auxiliary optical unit 30. The ellipsoidal mirror 28 converges the reflected pulsed light from the sample 8. The planar mirror 29 is located between the ellipsoidal mirror 28 and the detector 12 and serves to deflect the reflected pulsed light from the ellipsoidal mirror 28. There may be one ellipsoidal mirror 28 and one planar mirror 29, as in the present embodiment, or a plurality thereof may be combined.

The ellipsoidal mirror 26, the planar mirror 27, the ellipsoidal mirror 28, the planar mirror 29, which are optical elements, and other unillustrated optical systems have an optical design such that they are optically aligned with respect to this auxiliary optical unit 30.

This embodiment is configured to detect a wave form signal of the electric field intensity of the reflected pulsed light from the sample. Of course, it may be configured to detect a wave form signal of the electric field intensity of transmitted pulsed light.

In the time-domain pulsed spectroscopy apparatus of the present invention, configured as described above in outline, preparations for sample measurement are carried out as follows.

First, the sample 8 to be measured is attached to the sample holder 31 in the auxiliary optical unit 30. Then, the auxiliary optical unit 30 is loaded in the time-domain pulsed spectroscopy apparatus 20. Then, in order to set an origin for the time-series position of an output signal for a specific optical path length in the sample-unit entrance and exit optical systems 32, 33, 34, 35, 36, and 37 inside this auxiliary optical unit 30, the driving device and computer control apparatus, which are not shown, are operated to scan the reflector 41 for setting the photometric range. Thus, preparations for sample measurement are completed.

The time-domain pulsed spectroscopy apparatus of the present invention also carries out sample measurement in substantially the same way as the conventional apparatus shown in FIG. 1.

More specifically, the pulsed laser light L1 emitted from the light source 1 is divided, by the splitting unit 2, into the excitation pulsed laser light (pump pulsed light) L2 and the detection pulsed laser light (sampling pulsed light) L3.

The excitation pulsed laser light L2 is radiated onto the pulsed-light emitting unit 5 via a lens 4. Due to this irradiation, the pulsed-light emitting unit 5 emits a far-infrared electromagnetic pulse. After this far-infrared electromagnetic pulse has its optical path deflected by the plane mirror 27, it is guided to the ellipsoidal mirror 26 where it is focused. The far-infrared electromagnetic pulse guided inside the auxiliary optical unit 30 is focused via the sample-unit entrance optical system 32, 33, and 34 and is radiated onto the sample 8. The reflected pulsed electromagnetic wave reflected from the sample 8, including optical information about the sample 8, is reflected, via the sample-unit exit optical system 35, 36, and 37, at the ellipsoidal mirror 28 outside the auxiliary optical unit 30, and is thereafter deflected at the plane mirror 29 and then guided to the detector 12.

On the other hand, the detection pulsed laser light L3 split off at the splitting unit 2 defines the conductivity of the detector 12 only at that instant and enables detection, as an electrical current, of the electric field intensity of the reflected pulsed electromagnetic wave arriving from the sample 8 at that instant. Here, by applying a delay time difference at predetermined time intervals to the detection pulsed laser light L3 with respect to the excitation pulsed laser light L2, it is possible to acquire a wave form signal of the electric field intensity of the reflected pulsed electromagnetic wave from the sample 8.

Although it is not illustrated in the drawings, this time-domain pulsed spectroscopy apparatus may be provided with a reflector exclusively for adjusting the temporal origin.

Therefore, according to the present embodiment, the pulsed light emitted from the pulsed-light emitting unit 5 is deflected by the plane mirror 27 disposed between the pulsed-light emitting unit 5 and the ellipsoidal mirror 26. Thus, it is possible to increase the optical path length of the pulsed-light emitting unit 5 and the ellipsoidal mirror 26 and the focal area of the beam focused by the ellipsoidal mirror 26 can be reduced as much as possible; consequently, the spatial resolution of the sample 8 to be measured can be improved.

Also, since the pulsed light is deflected by the plane mirror 27, as well as increasing the optical path length, it is also possible to make the apparatus configuration extremely compact.

Furthermore, because the optical path length of the pulsed-light emitting unit 5 and the ellipsoidal mirror 26 can be increased, it is possible to increase the distance between the ellipsoidal mirror 26 and the sample 8 while maintaining the desired focal area. Accordingly, sufficient space can be secured for installing the auxiliary optical unit 30, thus facilitating analysis.

Similarly to the incident-side optical path, the detection-side optical path between the detector 12 and the auxiliary optical unit 30 is configured such that the planar mirror 29 is disposed between the ellipsoidal mirror 28 and the detector 12 to increase the optical path length; therefore, the focal area of the light beam converged by the ellipsoidal mirror 28 can be reduced as much as possible, and consequently, it is possible to improve the spatial resolution of the sample 8 to be measured. Furthermore, similarly to the incident-side optical path, the apparatus configuration can be made compact, and a sufficient space for installing the auxiliary optical unit 30 can be ensured.

Figure 3A:
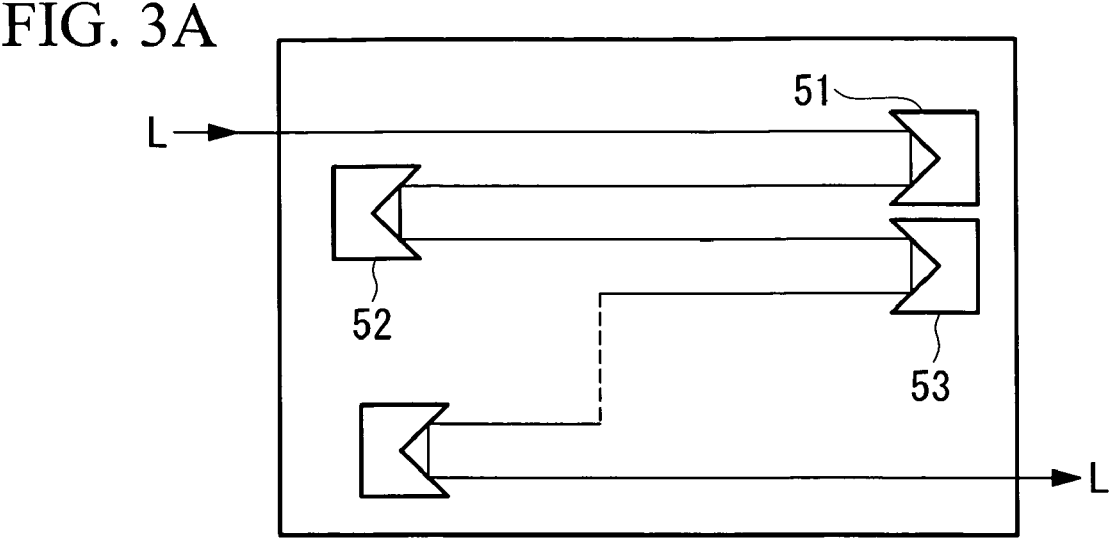
[FIG. 3](a) Outline configuration diagram of an embodiment of an optical-path-difference compensation mechanism for wave form signal acquisition in the time-domain pulsed spectroscopy apparatus of the present invention. (b) Diagram showing a configuration in which configurations shown in (a) are disposed in parallel.
Figure 3B:
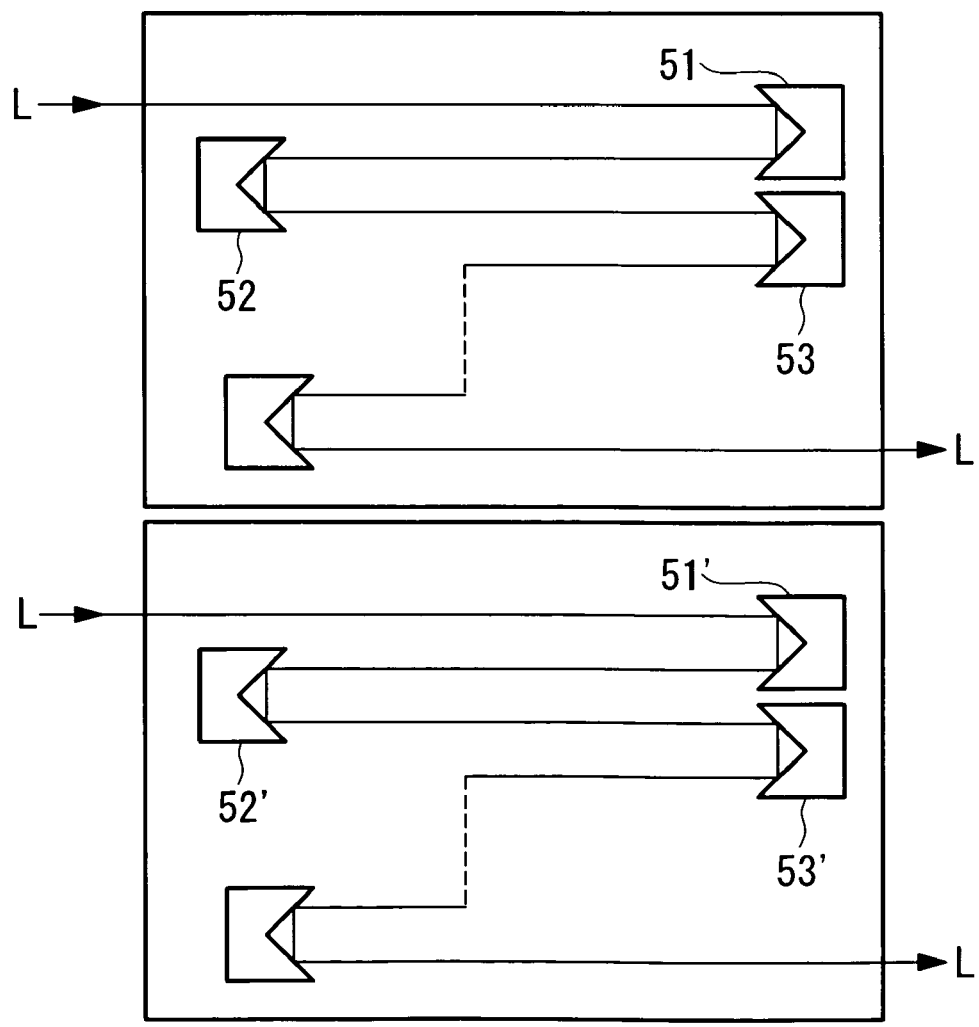

FIG. 3(*a*) shows the outline configuration of another embodiment of an optical-path-difference compensation mechanism for wave form signal acquisition of the time-domain pulsed spectroscopy apparatus of the present invention.

In this embodiment, in the incident-side optical path from the splitting unit to the pulsed-light emitting unit and/or in the detection-side optical path from the splitting unit to the detector, a plurality of optical-path-length varying units and/or optical delay units (reflectors in the case of FIG. 3) are disposed opposite each other such that the paths of light incident on and reflected from the reflectors are parallel and the optical paths are staggered. In the case shown in the figure, the reflectors are corner cube mirrors. In this configuration, the pulsed laser light L2 or L3 incident on the scanning mechanism are sequentially reflected at corner cube mirrors 51, 52, 53, . . . , guided outside the scanning mechanism, and sent to the pulsed-light emitting unit 5 or the detector 12.

Due to this configuration, compared to the case of a single reflector, the optical path length can be varied by amounts according to the number of reflectors. Also, according to this configuration, it is possible to greatly vary the optical path length in a case where there is insufficient space in the scanning direction of the reflector but where there is sufficient space in a direction orthogonal to the scanning direction. In this embodiment, as shown in FIG. 3(*b*), scanning mechanisms with a configuration like that in FIG. 3(*a*) may be disposed in parallel in the incident-side optical path and/or the detection-side optical path.

As shown in FIG. 3(*b*), optical-path-length varying units and/or optical delay units with a configuration like that in FIG. 3(*a*) may be disposed in parallel in the incident-side optical path and/or the detection-side optical path.

Figure 4:
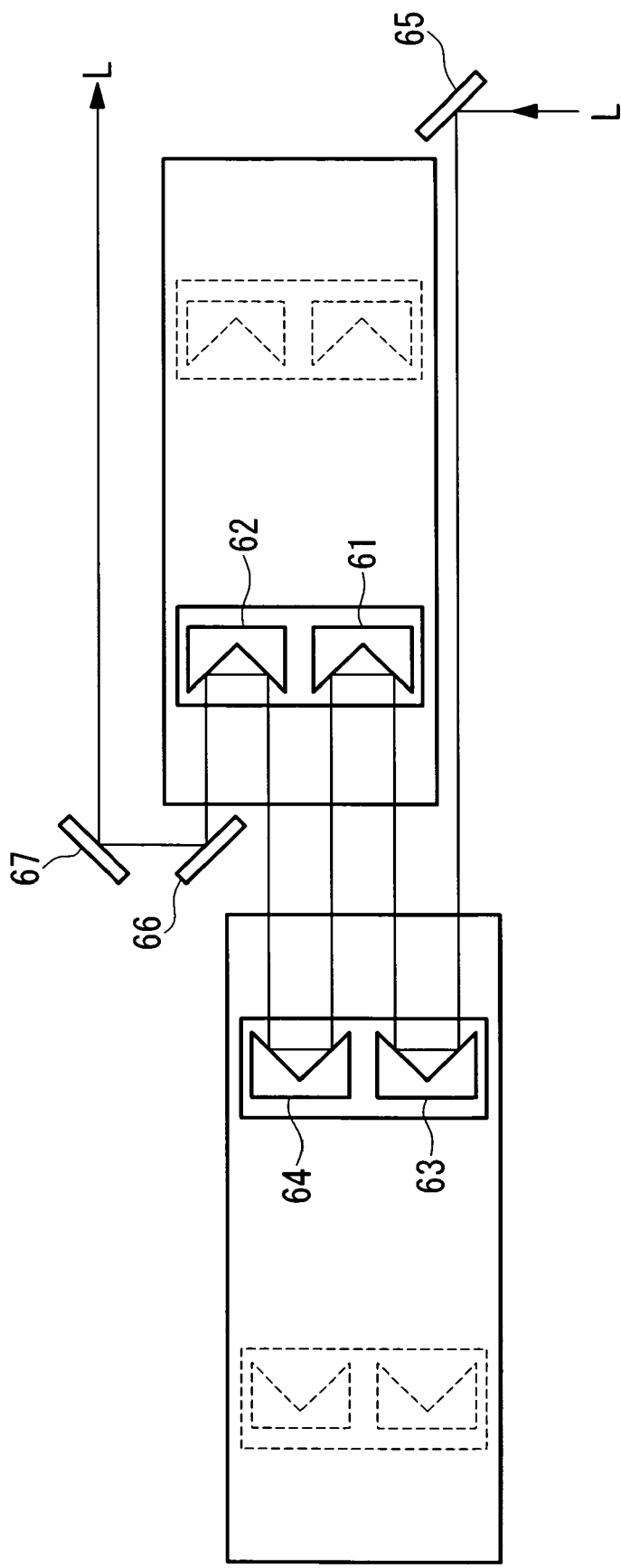
[FIG. 4] Outline configuration diagram of another embodiment of an optical-path-difference compensation mechanism for wave form signal acquisition in the time-domain pulsed spectroscopy apparatus of the present invention.

FIG. 4 shows the outline configuration of another embodiment of an optical-path-difference compensation mechanism for wave form signal acquisition in the time-domain pulsed spectroscopy apparatus of the present invention.

This embodiment is configured such that two reflectors for setting the photometric range (corner cube mirrors in the figure) and two reflectors for wave form signal measurement (corner cube mirrors in the figure) (61 and 62, and 63 and 64) are aligned and scanned simultaneously, and the reflectors 61 and 62 for setting the photometric range and the reflectors 63 and 64 for wave form signal measurement are disposed opposite each other such that the optical paths are staggered. In this configuration, the excitation pulsed light L2 or the detection pulsed light L3, split into two by the splitting unit, is reflected by the mirror 65; thereafter, it enters the scanning mechanism, is reflected in turn at the reflectors 63, 61, 64, and 62 for setting the photometric range and for wave form signal measurement, is guided outside the scanning mechanism, and is then reflected at the mirrors 66 and 67 and sent to the pulsed-light emitting unit 5 and the detector 12.

This configuration, compared to the case of a single corner cube mirror, has the feature that the optical path length can be changed by a factor of two relative to the scanning of the reflector. Therefore, an advantage is provided in that photometric range setting and setting for wave form signal measurement can be performed quickly. The configuration in FIG. 4 may be used in either the optical-path-length varying unit or the optical delay unit.

Figure 5A:
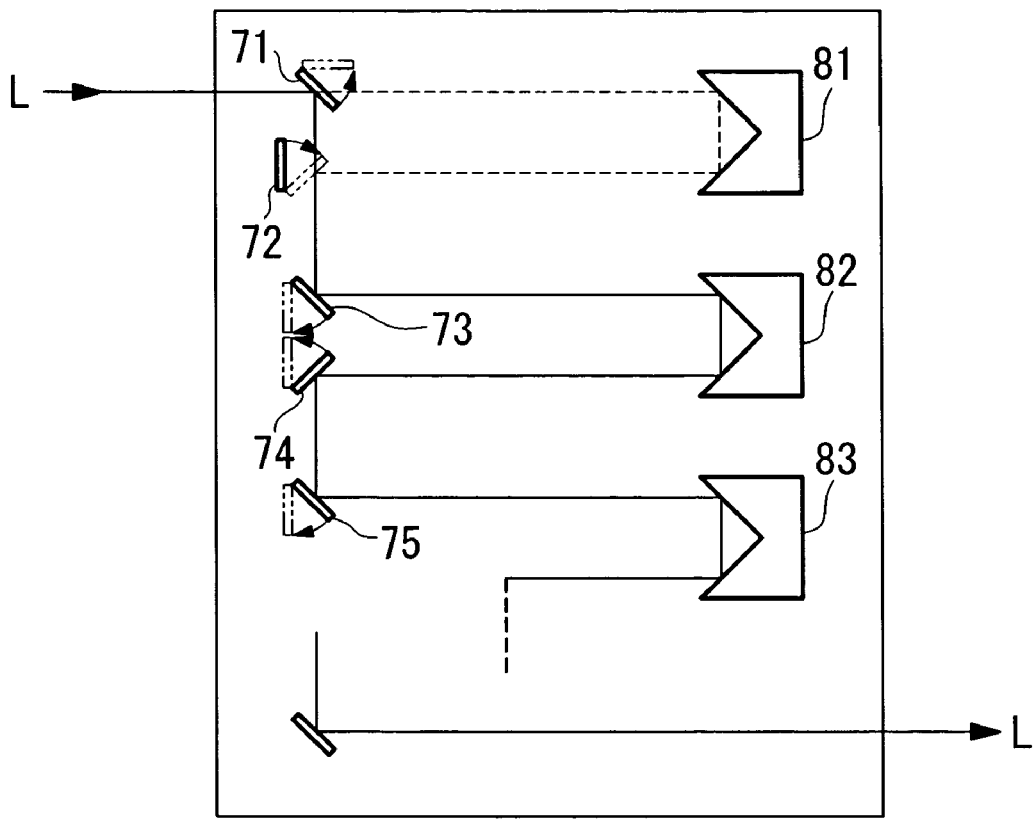
[FIG. 5](a) Outline configuration diagram of another embodiment of an optical-path-difference compensation mechanism for wave form signal acquisition in the time-domain pulsed spectroscopy apparatus of the present invention. (b) Magnified view of part of (a).
Figure 5B:
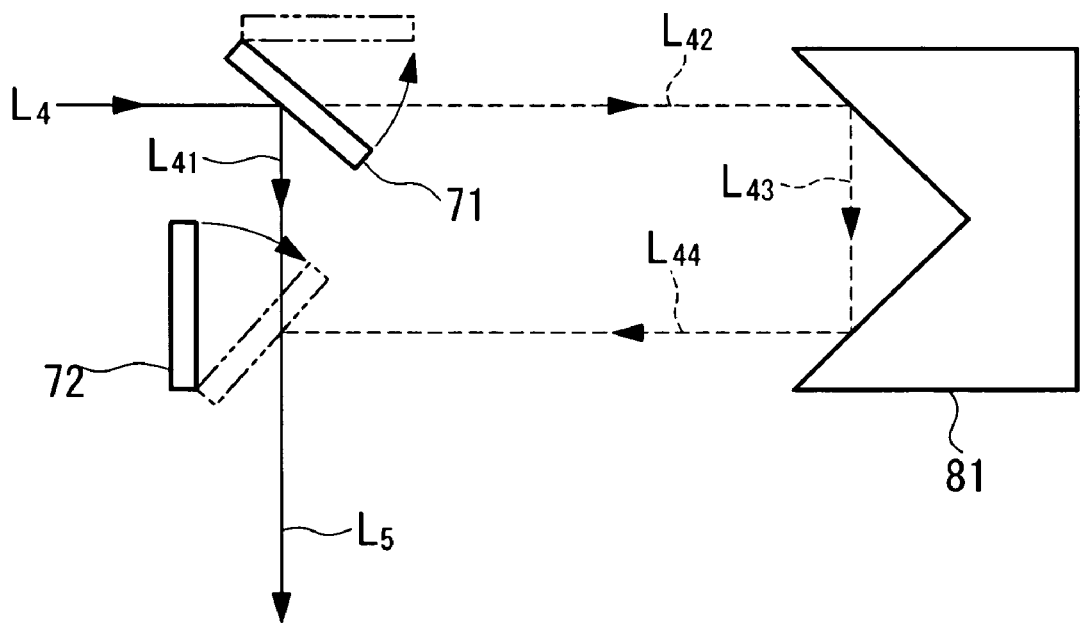

FIG. 5(*a*) shows an outline configuration of another embodiment of an optical-path-difference compensation mechanism for acquiring a wave form signal in the time-domain pulsed spectroscopy apparatus of the present invention.

In the embodiment in FIG. 5(*a*), optical-path-length varying units 81, 82, 83, . . . for setting the measurement range are movable or fixed reflectors, and by providing any of these reflectors with gate members 71, 73, and 75 for passing or blocking pulsed light to these reflectors, at least at the incident side of the pulsed light to these reflectors, and switching between these passing or blocking modes, it is possible to add optical paths via one, two, or more of the reflectors 81, 82, 83, . . . to extend the optical path length, and/or it is possible to skip one, two, or more of the reflectors 81, 82, 83, . . . to shorten the optical path length. Also, in the case shown in FIG. 5, the gate members are reflecting mirrors, and reflecting mirrors 72, 74, . . . for reflecting the pulsed light reflected from the reflectors 81, 82, 83, . . . towards the adjacent reflectors are provided. In this embodiment, the passage or blocking of at least one reflecting mirror (gate member) is carried out by inserting it into and removing it from the optical path of the reflecting mirror by rotation of the reflecting mirror. In the figure, the arrows in the vicinity of the reflecting mirrors and the solid lines and dotted lines indicating the reflecting mirrors schematically illustrate switching between the passing and blocking states of the reflecting mirrors.

The operation of this embodiment will be described using FIG. 5(*b*), which is an enlarged view of part of FIG. 5(*a*). For example, before switching, when the reflecting mirror 71 is inserted into the optical path (solid line) and the reflecting mirror 72 (solid line) is removed from the optical path, the laser light L4 is reflected at the reflecting mirror 71, becomes L41, and proceeds as L5. In such a case, the reflector 81 is skipped. In contrast, when the reflecting mirrors 71 and 72 are switched and the reflecting mirror 71 is removed from the optical path and the reflecting mirror 72 is inserted into the optical path, as shown by the dotted lines, the laser light L4 is reflected, as L42, at the reflector 81, becomes L43, is reflected again, becomes L44, is reflected at the reflecting mirror 72, and proceeds as L5. By switching in this way, an optical path length via the reflector 81 is added. Accordingly, if this switching order is reversed, conversely, the optical path via the reflector 81 is eliminated, and the optical path length is reduced. The configuration in FIG. 5 may be used in either the optical-path-length varying unit or the optical delay unit.

Figure 6:
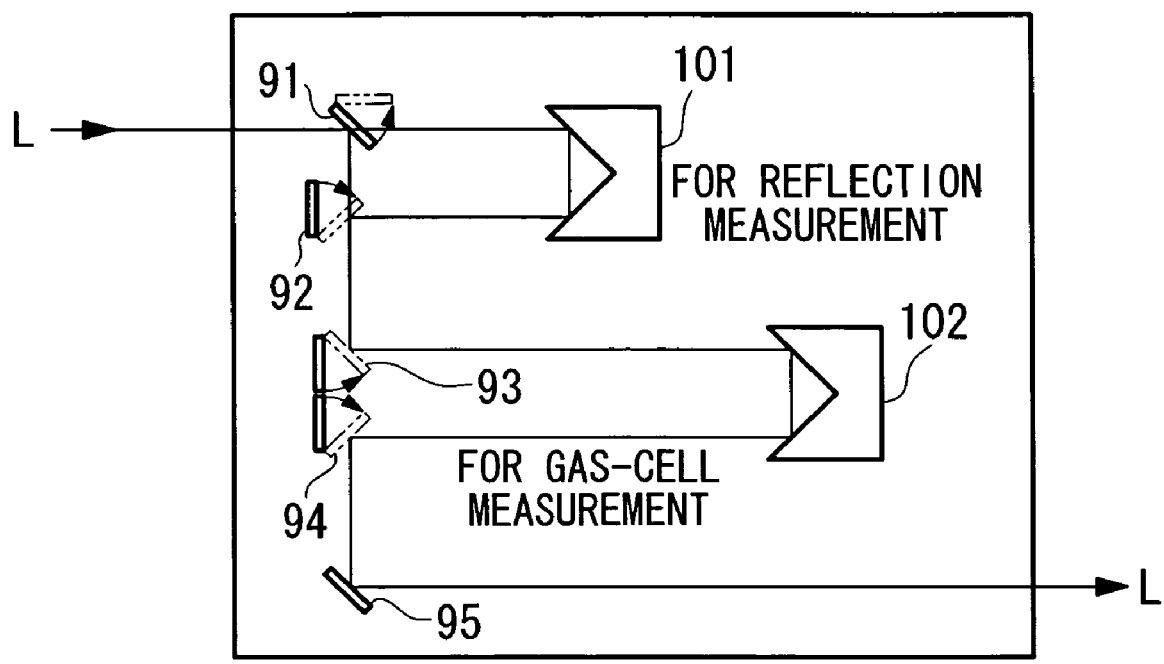
[FIG. 6] Outline configuration diagram of another embodiment of an optical-path-difference compensation mechanism for wave form signal acquisition in the time-domain pulsed spectroscopy apparatus of the present invention.

FIG. 6 shows the outline configuration of another embodiment of an optical-path-difference compensation mechanism for acquiring a wave form signal in the time-domain pulsed spectroscopy apparatus of the present invention.

This embodiment has a configuration in which a plurality of reflectors 101, 102, . . . are disposed in appropriate positions according to the application, and the optical path length is varied by gate members 91, 93, . . . and reflecting mirrors 92, 94, . . . for sending light to the adjacent reflectors. In the case shown in FIG. 6, the gate members are reflecting mirrors.

In this embodiment, when the gate members 91, 93, . . . and the reflecting mirror 92, 94, . . . for sending light to the adjacent reflectors are disposed at the solid-line positions, the pulsed light incident on the optical-path-length varying unit is first reflected at the gate member 91, passes near the reflecting mirror 92, the gate member 93, and the reflecting mirror 94, and is reflected at the reflecting mirror 95 to be guided outside. In this case, measurement of the sample is not carried out using the reflectors 101 and 102. On the other hand, by switching the gate member 91 and the reflecting mirror 92 to the dotted-line positions, it is possible, with the pulsed light, to measure the sample using the reflector 101 (reflection measurement in the figure). Furthermore, by switching the gate member 91 and the reflecting mirror 92 to the solid-line positions and switching the gate member 93 and the reflecting mirror 94 to the dotted-line positions, it is possible to measure the sample using the reflector 102 (gas-cell measurement in the figure).

FIG. 7(a) and FIG. 7(b) show the outline configuration of another embodiment of an optical-path-difference compensation mechanism for acquiring a wave form signal in the time-domain pulsed spectroscopy apparatus.

In this embodiment, passing or blocking of at least one gate member 112 is performed by inserting it into and removing it from the optical path by translating the gate member 112. In particular, in the case shown in FIG. 7, the gate member 112 and a reflector 115 are provided together on a motion apparatus 116. Furthermore, a reflecting mirror 113 for reflecting and forwarding pulsed light reflected from the reflector 115 towards a reflecting mirror 114 is provided on the motion apparatus 116. In the case shown in the figure, the gate member 112 is a reflecting mirror.

In this case, when the motion apparatus is disposed at the position in FIG. 7(a), the pulsed light reflected from the reflecting mirror 111 passes near the gate member 112 and the reflecting mirror 113 and is reflected at the reflecting mirror 114 to be guided outside. When the motion apparatus 116 is moved from the position in FIG. 7(a) to the position in FIG. 7(b), the gate member 112, the reflecting mirror 113, and the reflector 115 are translated together, thus adding the optical path via the reflector 115 to extend the optical path length, which enables measurement using the reflector 115.

The invention claimed is:

1. A time-domain pulsed spectroscopy apparatus comprising:
    a pulsed laser light source;
    a splitting unit configured to split pulsed laser light from the pulsed laser light source into excitation pulsed laser light and detection pulsed laser light;
    a pulsed-light emitting unit configured to emit pulsed light including wavelengths in the far-infrared wavelength region due to irradiation of the excitation pulsed laser;
    a detector configured to detect a wave form signal of the electric field intensity of reflected or transmitted pulsed light from the sample onto which the pulsed light from the pulsed-light emitting unit is radiated;
    a sample holder configured to hold the sample; and
    sample-unit entrance and exit optical systems configured to guide the pulsed light from the pulsed-light emitting unit to the sample and to guide to the detector pulsed light reflected from or transmitted through the sample due to the irradiation,
    wherein the time-domain pulsed spectroscopy apparatus further comprises:
    at least one optical-path-length varying unit, disposed in an incident-side optical path from the splitting unit to the pulsed-light emitting unit and/or in a detection-side optical path from the splitting unit to the detector
    wherein the optical-path-length varying unit for setting a photometric range is a reflector that is either moveable or fixed; and,
    said reflector includes, at the incident side of the pulsed light to the reflector, a gate member configured to pass or block the pulsed light to the reflector by blocking to add an optical path via the reflector to extend the optical path length or passing to skip the reflector to shorten the optical path length.

2. A time-domain pulsed spectroscopy apparatus according to claim 1, wherein the optical-path-length varying unit for setting a photometric range is a movable reflector.

3. A time-domain pulsed spectroscopy apparatus according to claim 1, wherein passing or blocking of at least one of the gate members is performed by inserting and removing the gate member, by translational motion, into and from the optical path.

4. A time-domain pulsed spectroscopy apparatus according to claim 1, wherein passing or blocking of at least one of the gate members is performed by inserting and removing the gate member, by rotation, into and from the optical path.

5. A time-domain pulsed spectroscopy apparatus according to claims 1, 2, 3, or 4, further comprising: a driving device configured to automatically scan the optical-path-length varying unit and/or the optical delay unit; and a computer control apparatus configured to automatically control the driving device.

6. A time-domain pulsed spectroscopy apparatus according to claim 1, wherein the sample holder and the sample-unit entrance and exit optical systems are provided inside an auxiliary optical unit that can be attached to and removed from the time-domain pulsed spectroscopy apparatus to enable replacement thereof.

7. A time-domain pulsed spectroscopy apparatus according to claim 6 having an optical design that provides optical alignment with respect to the auxiliary optical unit.

8. A time-domain pulsed spectroscopy apparatus according to claim 1 wherein, in the time-domain pulsed spectroscopy apparatus comprising:

a pulsed laser light source;

a splitting unit configured to split pulsed laser light from the pulsed laser light source into excitation pulsed laser light and detection pulsed laser light;

a pulsed-light emitting unit configured to emit pulsed light including wavelengths in the far-infrared wavelength region due to irradiation of the excitation pulsed laser;

a detector configured to detect a wave form signal of the electric field intensity of reflected or transmitted pulsed light from the sample onto which the pulsed light from the pulsed-light emitting unit is radiated;

a sample holder configured to hold the sample; and sample-unit entrance and exit optical systems configured to guide the pulsed light from the pulsed-light emitting unit to the sample and to guide to the detector pulsed light reflected from or transmitted through the sample due to the irradiation, from the pulsed-light emitting unit to the sample-unit entrance and exit optical systems and/or from the detector to the sample-unit entrance and exit optical systems, one or a plurality of planar mirrors and one or a plurality of aspherical mirrors are disposed in this order.

* * * * *